US00PP35553P2

(12) United States Plant Patent
Rouwette

(10) Patent No.: US PP35,553 P2
(45) Date of Patent: Dec. 19, 2023

(54) ***HYDRANGEA* PLANT NAMED 'GRHP12'**

(50) Latin Name: *Hydrangea paniculata*
Varietal Denomination: GRHP12

(71) Applicant: Guido Rouwette, Valkenburg (NL)

(72) Inventor: Guido Rouwette, Valkenburg (NL)

( * ) Notice: Subject to any disclaimer, the term of this patent is extended or adjusted under 35 U.S.C. 154(b) by 0 days.

(21) Appl. No.: 18/098,088

(22) Filed: Jan. 17, 2023

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./250
See application file for complete search history.

(56) References Cited

PUBLICATIONS https://pluto.upov.int/result (citation for 'GRHP12'; Retrieved from the Internet on May 9, 2023; 1 page total).*

* cited by examiner

*Primary Examiner* — Susan McCormick Ewoldt
(74) *Attorney, Agent, or Firm* — Penny J Aguirre

(57) ABSTRACT

A new cultivar of *Hydrangea paniculata* plant named 'GRHP12' that is characterized by its flower panicles that change in color from lime green and white to green and pink to dark cherry pink as they mature, its well-branched plant habit with sturdy stems, its floriferous blooming habit, its dense and sturdy flower panicles, and its large flower panicles with rounded, large sepals.

3 Drawing Sheets

Botanical classification: *Hydrangea paniculata.*
Varietal denomination: 'GRHP12'.

BACKGROUND OF THE INVENTION

The present invention relates to a new and distinct cultivar of *Hydrangea paniculata* and will be referred to hereafter by its cultivar name, 'GRHP12'. 'GRHP12' represents a new panicle *Hydrangea*, a perennial shrub grown for landscape use.

The new *Hydrangea* resulted from a controlled breeding program conducted by the Inventor in Valkenburg, The Netherlands. Goals of the breeding program were to develop new cultivars of *Hydrangea paniculata* with sturdy stems, healthy foliage, and unique flower colors. The Inventor made crosses in 2009 between unnamed and unpatented proprietary plants of *Hydrangea paniculata* in the Inventor's breeding program as both the female and male parents. The exact characteristics of the parents are unknown as seeds were pooled and sown from several crosses. 'GRHP12' was selected as a single unique plant in summer of 2012 from the resulting seedlings of the above crosses.

Asexual propagation of the new cultivar was first accomplished using stem cuttings by the Inventor in summer of 2012 in Valkenburg, The Netherlands. Asexual propagation using stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'GRHP12' as a unique cultivar of *Hydrangea.*

1. 'GRHP12' exhibits inflorescences with flower panicles that change in color from lime green and white to green and pink to dark cherry pink as they mature.
2. 'GRHP12' exhibits a well-branched plant habit with sturdy stems.
3. 'GRHP12' exhibits a floriferous blooming habit.
4. 'GRHP12' exhibits dense and sturdy flower panicles.
5. 'GRHP12' exhibits large flower panicles with rounded, large sepals.

'GRHP12' can be most closely compared to the *Hydrangea paniculata* cultivars 'Limelight' (U.S. Plant Pat. No. 12,874), 'DVP Pinky' (U.S. Plant Pat. No. 16,166), and 'GRHPLF'. 'Limelight' is similar to 'GRHP12' in having dense flower panicles, a well-branched plant habit, a floriferous blooming habit, and a similar plant size. 'Limelight' differs from 'GRHP12' in having inflorescences with flower panicles that change in color from white with lime-green to lighter pink tones later in the season and sterile sepals that are smaller in size. 'Pinky Winky' is similar to 'GRHP12' in having a well-branched plant habit. 'Pinky Winky' differs from 'GRHP12' in having flower panicles that are less dense, smaller, more pointed in shape and in being more white in color (lacking green) with less pink coloration when container grown.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Plantipp (the breeder's representative for licensing, Visions (photographs only), Persishable News, Globeplanter, KVBC, Groot-GroenPlus, Boom In Business, dergartenbasu, Flora News, Gabot, Varb, and SZKOLKARSTWO.

BRIEF DESCRIPTION OF THE DRAWINGS

The accompanying color photographs illustrate the overall appearance and distinct characteristics of the new *Hydrangea*. The photographs were taken of three-year-old plants of 'GRHP12' grown outdoors in a trial field in Valkenburg, The Netherlands.

The photograph in FIG. 1 provides a view of several plants of 'GRHP12' (center) in bloom in fall.

Figure 1:
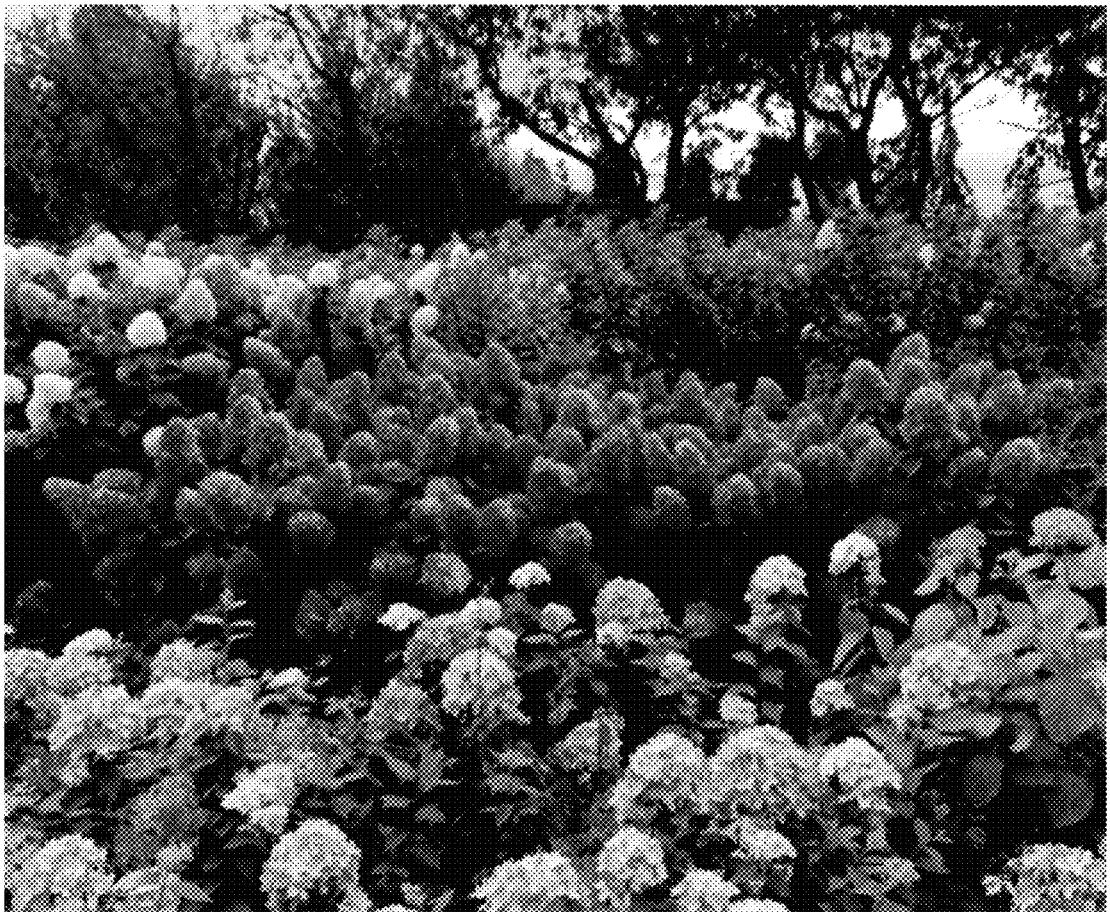
Figure 2:
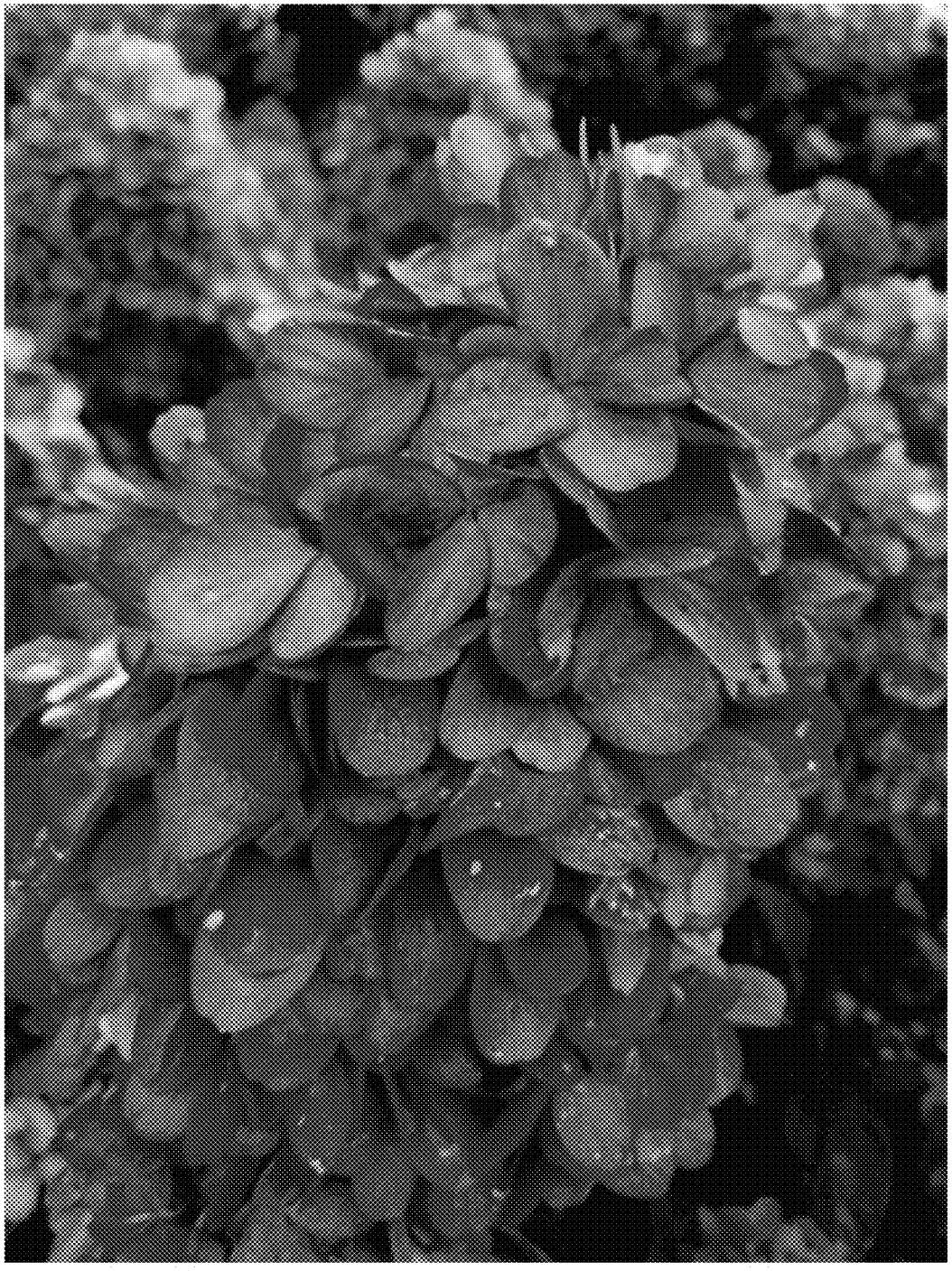

The photograph in FIG. 2 provides a close-up view of an inflorescence of 'GRHP12' in fall.

Figure 3:
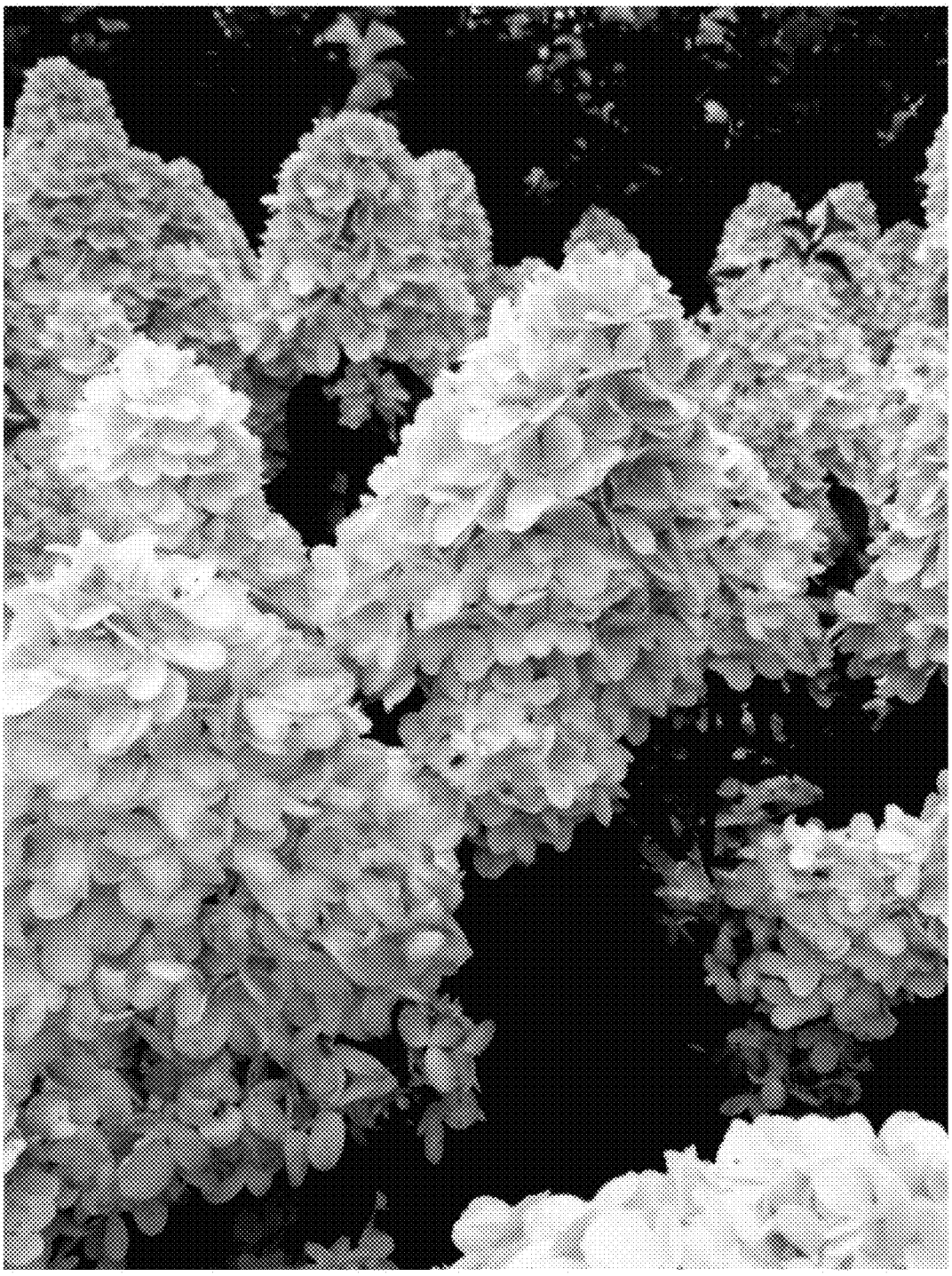

The photograph in FIG. 3 provides a close-up view of an inflorescence of 'GRHP12' in late summer.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of 2.5-year-old plants of 'GRHP12' as grown outdoors in a trial garden in Vorden, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Mid-summer through autumn in The Netherlands.

*Plant type*.—Deciduous shrub, panicle type *Hydrangea*.

*Plant habit*.—Medium size, dense, and upright.

*Height and spread*.—Reaches 100 to 120 cm in height and spread ion the landscape.

*Hardiness*.—At least in U.S.D.A. Zones 4 to 9.

*Diseases and pests*.—No susceptibility and resistance to diseases or pests has been observed.

*Root description*.—Fibrous, NN155A and 164A in color.

*Propagation*.—Stem cuttings.

*Root development*.—6 to 8 weeks for root initiation with a finished plant produced in in a P9 container in about 12 months from a rooted cutting.

*Growth rate and vigor*.—Moderate.

Stem description:

*Stem shape*.—Rounded.

*Stem strength*.—Strong.

*Stem color*.—Young; 145B, mature; 200C, old bark; N199B.

*Stem size*.—Average of 66 cm in length (excluding inflorescence) and 8 mm in diameter.

*Stem surface*.—Stems are slightly pubescent and covered with lenticels an average of 2 mm in length, mature bark is mostly smooth and lacks fasciation.

*Internode length*.—An average of 5 cm.

*Branching*.—Freely branching with an average of 15 lateral branches, sturdy.

Foliage description:

*Leaf shape*.—Ovate.

*Leaf arrangement*.—Opposite.

*Leaf division*.—Simple.

*Leaf base*.—Obtuse.

*Leaf apex*.—Acute.

*Leaf margins*.—Serrate.

*Leaf venation*.—Pinnate, color; upper surface 145B, lower surface 145B to 145C.

*Leaf size*.—An average of 15.2 cm in length and 7.3 cm in width.

*Leaf attachment*.—Petiolate.

*Leaf surface*.—Both surfaces; matte, and pubescent.

*Leaf color*.—Young upper surface; 137A, young lower surface 137C, mature upper surface 137B, mature lower surface 137C to 137D.

*Petioles*.—An average of 2.1 mm in length and 3 mm in diameter, both surfaces matte and slightly pubescent, color 145D and 187B to 187C.

Inflorescence description:

*Inflorescence type*.—Terminal conical panicle, comprised of sterile and fertile flowers.

*Lastingness of inflorescence*.—Sterile flowers; persistent for an average of 6 weeks, fertile flowers; self-cleaning, an average of 5 days.

*Inflorescence number*.—One per lateral stem.

*Inflorescence size*.—An average of 24 cm in height and 20 cm in diameter.

*Flower number*.—An average of 300 sterile flowers and 150 fertile flowers per panicle.

*Flower fragrance*.—None.

*Flower size*.—Sterile flowers; up to 5 cm in diameter and 1.2 m in depth, fertile flowers; an average of 5 mm in diameter and 3 mm in depth.

*Flower type*.—Rotate.

*Flower buds*.—Sterile flowers; an average of 2 mm in length and diameter, round in shape, 145D, fertile flowers; an average of 3 mm in length and diameter, ovoid in shape, 145C to 145D in color.

*Petals*.—Sterile flowers; petals do not open and remain in bud stage, fertile flowers; 5, rotate and cruciform in shape, ovate in shape, acute apex, cuneate base, entire margins, average of 3 mm in length and 1.5 mm in width, both surfaces glabrous and slightly glossy, color; when opening and fully open upper and lower surface NN155D.

*Peduncles*.—Primary peduncles; strong, flattened oval in shape, an average of 3 cm in length and 2 mm in width. secondary peduncles 2 cm in length and 2 mm in width, 145C to 145D in color, surface is matte and pubescent.

*Pedicels*.—Sterile flowers; moderate strength, an average of 1.8 cm in length and 1 mm in width, 145D in color, surface is matte and pubescent, fertile flowers; moderate strength, an average of 2 mm in length, 1 mm in diameter, 145C to 145D in color, surface is matte and slightly pubescent.

*Sepals*.—Sterile flowers; 4 to 5, rotate, elliptic to ovate in shape, obtuse apex, acute base, entire margins, average of 2.2 cm in length and 1.7 cm in width, both surfaces glabrous and matte, color: upper and lower surface when opening; 145B to 145C, upper surface when fully open; 145C to 145D, later in the season sepals change to NN155D and 145D with flushes of 63A, as the sepals mature they start to become 60A to 60B, becoming fully 60A to 60B in autumn, lower surface when fully open; 145C to 145D with 60C to 60D, fertile flowers; 5, rotate, ovate in shape, acute apex, broad cuneate base, entire margins, 2 mm in length, 1 mm in width, both surfaces glabrous and matte, color: when opening and fully open upper and lower surface; NN155D.

Reproductive organs:

*Gynoecium*.—Sterile flowers; flowers do not open, fertile flowers; 1 pistil, an average of 2 mm in length, stigma; club-shaped and 157B in color, style; 1 mm in length, NN155D in color, ovary is 157D in color.

*Androecium*.—Sterile flowers; flowers do not open, fertile flowers; stamens; average of 10, filaments; 3 mm in length, NN155D in color, anthers; broad oblong in shape, 1 mm in length, 155D in color, pollen; low to moderate quantity, 156C in color.

*Fruit and seed*.—None observed to date.

It is claimed:

1. A new and distinct cultivar of *Hydrangea* plant named 'GRHP12' substantially as herein illustrated and described.

* * * * *